United States Patent [19]

Puttner et al.

[11] 3,956,307

[45] May 11, 1976

[54] BENZIMIDAZOLE-1-CARBOXIMIDIC ACID ESTERS

[75] Inventors: Reinhold Puttner; Kurt Röder; Ernst A. Pieroh, all of Berlin, Germany

[73] Assignee: Schering Aktiengesellschaft, Berlin, Germany

[22] Filed: Oct. 1, 1974

[21] Appl. No.: 511,092

[30] Foreign Application Priority Data
Oct. 2, 1973  Germany............................ 2349919

[52] U.S. Cl.............................. 260/309.2; 424/273
[51] Int. Cl.².................................... C07D 235/32
[58] Field of Search.............................. 260/309.2

[56] References Cited
UNITED STATES PATENTS

| | | | |
|---|---|---|---|
| 3,626,070 | 12/1971 | Soboczenski | 260/309.2 |
| 3,631,176 | 12/1971 | Klopping | 260/309.2 |
| 3,751,425 | 8/1973 | Osieka et al. | 260/309.2 |

FOREIGN PATENTS OR APPLICATIONS

| | | | |
|---|---|---|---|
| 1,523,597 | 3/1968 | France | 260/309.2 |

OTHER PUBLICATIONS

Grigat et al. I Chem. Ber. 1964, Vol. 97, pp. 3027–3035.
Grigat et al. II Chem. Abst. 1965, Vol. 62, columns 5221–5222.
Ferbenfabriken Bayer A.-G. Chem. Abst. 1965, Vol. 62, column 14697.

*Primary Examiner*—Natalie Trousoe
*Attorney, Agent, or Firm*—Joseph F. Padlon

[57] ABSTRACT

The specification discloses esters of benzimidazole-1-carboximidic acids having antifungal properties and the use of these compounds for the protection of crops and plants from attack by fungi.

2 Claims, No Drawings

BENZIMIDAZOLE-1-CARBOXIMIDIC ACID ESTERS

The invention concerns new benzimidazole-1-carboximidic acid esters, and the methods for the production of these compounds, to agents having fungicidal and insecticidal action containing these compounds as active substances.

The fungicidal action of benzimidazole derivatives is known. One of their most important representatives is methyl-1-(butylcarbamoyl)-2-benzimidazole carbamate, which is already introduced into the practice of controlling phytopathogenic fungi (cf. French Pat. No. 1,523,359). Although this active substance has a broad spectrum of action, it does not always meet the requirements particularly concerning the systemic and prophylactic control of noxious fungi in agricultural and other cultivations.

The object of the present invention therefore is to provide an agent of superior systemic and prophylactic fungicidal effect against noxious fungi and for use in agricultural and other cultivations.

This problem is solved according to the invention by an agent which is characterized by a content of at least one compound of the general formula

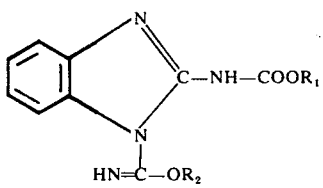

in which $R_1$ is an aliphatic hydrocarbon radical with 1 to 4 carbon atoms and $R_2$ is a trihalogen alkyl group, an aromatic hydrocarbon radical, mono- or poly-substituted by an aliphatic hydrocarbon radical, an aromatic hydrocarbon radical, a cycloaliphatic hydrocarbon radical, an alkoxy radical, an alkyl thio radical, an alkoxycarbonyl radical, an acyl radical, an acylamido radical, a dialkylamino radical, a trifluoromethyl group, the nitro group, the nitrile group or halogen, identical or different, or the radical

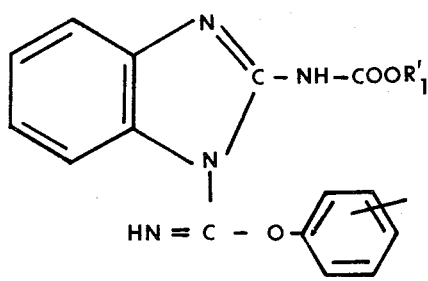

where $R'_1$ has the meaning of $R_1$.

By the aliphatic hydrocarbon radical designated as $R_1$ in the general formula is understood methyl, ethyl, propyl, isopropyl, n-butyl, sec.-butyl and allyl, compounds with $R_1$ in the meaning of methyl, ethyl and isopropyl being outstanding in their fungicidal effect.

The radicals designated as $R_2$ must be understood to include under the trihalogen alkyl group the 2,2,2-trifluoro-ethyl group, the 2,2,2-trichloroethyl group and the 2,2,2-tribromoethyl group. As aromatic hydrocarbon radicals should be mentioned e.g. the phenyl, 1-naphthyl and 2-naphthyl radical, which may be mono- or poly-substituted, identically or differently. Examples of substituents are:

Aliphatic hydrocarbon radicals with 1 to 12 carbon atoms, such as methyl, ethyl, propyl, isopropyl, sec.-butyl, tert.-butyl, allyl, nonyl, and others; aromatic hydrocarbon radicals, such as phenyl; cycloaliphatic hydrocarbon radicals, such as cyclohexyl; halogens, such as fluorine, chlorine and bromine; alkoxy radicals, such as methoxy; alkyl thio radicals, such as methylthio; alkoxy carbonyl radicals, such as methoxy and ethoxy carbonyl; acyl radicals, such as formyl and acetyl; acylamido radicals, such as acetamido; dialkylamino radicals, such as dimethylamino, the trifluoromethyl group, the nitrile group, and the nitro group. Besides, $R_2$ may represent the groups

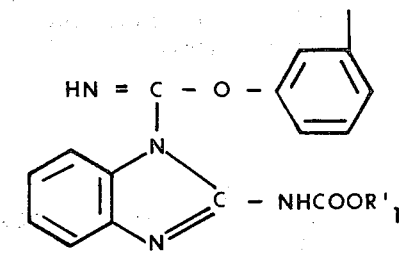

and

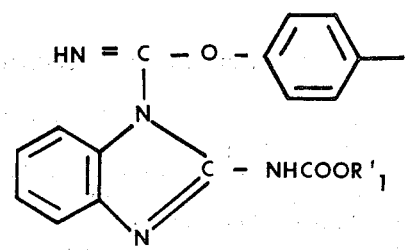

$R'_1$ having the above mentioned meaning of $R_1$.

Illustrative compounds are those in which $R_1$ is alkyl or alkenyl each having from 1 to 4 carbons and $R_2$ is selected from the group consisting of trihalolower alkyl, phenyl, naphthyl, phenyl mono-, di-, or tri-substituted with alkyl or alkenyl each having from 1 to 12 carbons, cyclohexyl, lower alkoxy, lower alkylthio, lower alkoxycarbonyl, lower alkanoyl, lower alkanoylamino, di loweralkylamino, trifluoromethyl, nitro, nitrile, halo, or the radicals

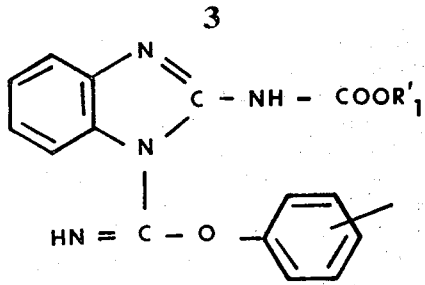

wherein $R'_1$ is methyl, ethyl, or isopropyl.

Another group of compounds includes those in which $R_1$ is methyl, ethyl or isopropyl and $R_2$ is 2,2,2,-trifluoroethyl, 2,2,2-trichloroethyl, 2,2,2-tribromoethyl, phenyl, methylphenyl, dimethylphenyl, trimethylphenyl, ethylphenyl, isopropylphenyl, tert.-butylphenyl, sec.-butylphenyl, isoheptylphenyl, nonylphenyl, biphenyl, naphthyl, chlorophenyl, fluorophenyl, bromophenyl, chloro-methylphenyl, bromomethyl-phenyl, methoxyphenyl, methylthiophenyl, methyl-methylthiophenyl, allylmethoxyphenyl, ethoxycarbonylphenyl, formylphenyl, acetylphenyl, acetamidophenyl, dimethylamino-phenyl, trifluoromethylphenyl, cyanophenyl, nitrophenyl or the radical

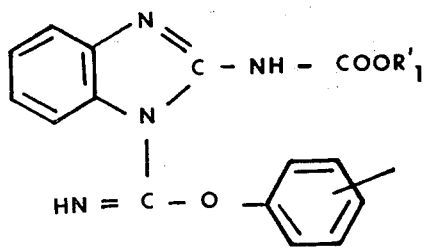

in which $R'_1$ has the meaning of methyl, ethyl or isopropyl.

The compounds according to the invention have eminent fungicidal properties. Thus they show good fungicidal effect against numerous noxious fungi, as for example Rhizoctonia, Fusarium, true mildew fungi, Piricularia, Botrytis, Fusicladium, etc.

As the compounds are practically non-toxic and excellently fruit- and plant-compatible, they can be used, among other things, in viniculture, fructiculture, ornamentals and in numerous crop cultivations, e.g. cotton, rice, and others.

The compounds of the invention have the special advantage of acting not only prophylactically but also curatively, so that established noxious fungi, such as Erysiphaceae, Venturia and Piricularia, cannot develop further. Moreover, the compounds exert a systemic effect, in that they are transported to the site of action in the sap stream of the plants. The absorption of the compounds occurs not only through the leaves, but also from the soil through the roots.

The compounds of the invention can therefore be used for example as sprays or as disinfectants in agriculture as well as in horticulture, etc. for the fungicidal treatment of infected or infection-endangered plants and soils or for the protection of seed.

In comparison to the known benzimidazole derivatives with fungicidal effect, as the methyl-1-(butylcarbamoyl)-2-benzimidazole carbamate of analogous constitution, some of the compounds of the invention have surprisingly proved effective also against biting and sucking noxious insects, for instance, against aphids, larvae of beetles and caterpillars of butterflies.

Application can be made either with an active substance alone or with mixtures of at least two active substances of different constitution from the group of the claimed compounds. If desired, other fungicides, nematocides, herbicides or other pest control agents can be added, depending on the desired purpose. Expediently, the active substances are employed in the form of preparations, such as powders, scatters, granulates, solutions, emulsions or suspensions, with addition of liquid and/or solid vehicles or diluents and possibly wetting, adhesion, emulsifying and/or dispersing aids. Suitable liquid vehicles are water, mineral oils or other organic solvents, as for example xylol, chlorobenzene, cyclohexanol, cyclohexanone, dioxane, acetonitrile, acetic ester dimethylformamide, isophorone and dimethyl sulfoxide, etc. Solid vehicles, such as lime, kaolin, chalk, talc, attaclay and other clays as well as natural or synthetic silicic acid. Among surface-active substances that may be used are salts of lignin sulfonic acid, salts of alkylated benzenesulfonic acids, sulfonated acid amides and their salts, polyethoxylated amines and alcohols.

If the active substances are to be used for seed disinfection, dyes may be admixed, to give the disinfected seed a distinctly visible coloration.

The proportion of active ingredient or ingredients in the agent may vary within wide limits and depends mainly on the quantity in which the agents are to be used for soil, seed or leaf treatment, among other things. As an example, the agents contain between about 1 and 80 per cent by weight, preferably between about 20 and 50 per cent by weight, active substance and about 99 to 20 per cent by weight liquid or solid vehicles plus optionally up to 20 per cent by weight surface-active substances.

The new compounds of the general formula (I) can be produced by reacting e.g. compounds of the general formula

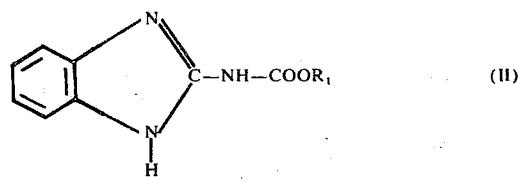 (II)

with cyanates of the general formula

$$R_2 - O - C \equiv N \qquad (III)$$

expediently in equimolecular quantity ratios in the presence of an inert organic solvent, $R_1$ and $R_2$ having the above mentioned meaning.

Solvents suitable for the reaction are acetone, chloroform and dimethyl sulfoxide.

It is obvious that in the case of the reaction of dicyanato compounds, one uses per equivalent of the compound of the general formula (II) only one half equivalent of the compound of the general formula (III).

The process products form in very good yield and purity and are isolated in a manner known in the art.

The following examples will explain the production of the compounds according to the invention.

1.

2-(Methoxycarbonylamino)-benzimidazole-1-carboximidic acid (3-methylphenyl) ester To a suspension of 9.56 g. (0.05 mole) 2-(methoxycarbonylamino)-benzimidazole in 300 ml chloroform a solution of 7.19 g (0.054 mole) 3-methylphenyl cyanate in 20 ml chloroform is added in drops while stirring at 20°C. The reaction mixture is stirred for 5 hours at room temperature and then filtered. The clear filtrate is concentrated under vacuum until dry. The colorless crystalline residue is treated with ether.

The yield is: 13.1 g = 81% of the theory
The m.p. is: 153°C (decomposition).

2.

2-(Methoxycarbonylamino)-benzimidazole-1-carboximidic acid phenyl ester.

To a suspension of 420.6 g (2.2 mole) 2-(methoxycarbonylamino)-benzimidazole in 10 ltr chloroform a solution of 274 g (2.3 moles) phenyl cyanate in 2 ltr chloroform is added in drops while stirring at 20°C. The reaction mixture is stirred for 6 hours at room temperature and then left standing overnight. The product is then filtered and the solvent removed under vacuum. The colorless, crystalline residue is treated with ether.

The yield is: 608 g = 89% of the theory
The m.p. is: 149°C (decomposition).

In the following table, additional compounds according to the invention are listed.

| Compound according to invention | Physical constant |
|---|---|
| 3. 2-(Isopropoxycarbonylamino)benzimidazole-1-carboximidic acid phenyl ester | M.p. 107–100°C |
| 4. 2-(Ethoxycarbonylamino)-benzimidazole-1-carboximidic acid phenyl ester | M.p. 147°C decompn. |
| 5. 2-(Methoxycarbonylamino)-benzimidazole-1-carboximidic acid-(2,2,2-trichloroethyl) ester | M.p. 160°C decompn. |
| 6. 2-(Ethoxycarbonylamino)-benzimidazole-1-carboximidic acid-(2,2,2-trichloroethyl) ester | M.p. 160°C decompn. |
| 7. 2-(Isopropoxycarbonylamino)-benzimidazole-1-carboximidic acid (2,2,2-trichloroethyl) ester | M.p. 150–154°C decompn. |
| 8. 2-(Methoxycarbonylamino)-benzimidazole-1-carboximidic acid-(2,2,2-trifluoroethyl) ester | M.p. 163°C decompn. |
| 9. 2-(Ethoxycarbonylamino)-benzimidazole-1-carboximidic acid-(2,2,2-trifluoroethyl) ester | M.p. 157°C decompn. |
| 10. 2-(Isopropoxycarbonylamino)-benzimidazole-1-carboximidic acid-(2,2,2-trifluoroethyl) ester | M.p. 152°C decompn. |
| 11. 2-(Methoxycarbonylamino)-benzimidazole-1-carboximidic acid-(2,2,2-tribromoethyl) ester | M.p. 203°C decompn. |
| 12. 2-(Ethoxycarbonylamino)-benzimidazole-1-carboximidic acid-(3-methylphenyl) ester | M.p. 155°C decompn. |
| 13. 2-(Isopropoxycarbonylamino)-benzimidazole-1-carboximidic acid-(3-methylphenyl) ester | M.p. 135–40°C. |
| 14. 2-(Methoxycarbonylamino)-benzimidazole-1-carboximidic acid-(2-methylphenyl ester | M.p. 142°C decompn. |
| 15. 2-(Ethoxycarbonylamino)-benzimidazole-1-carboximidic acid-(2-methylphenyl) ester | M.p. 145°C decompn. |
| 16. 2-(Isopropoxycarbonylamino)benzimidazole-1-carboximidic acid-(2-methylphenyl) ester | M.p. 170°C decompn. |
| 17. 2-(Methoxycarbonylamino)benzimidazole-1-carboximidic acid-(4-methylphenyl) ester | M.p. 145°C decompn. |
| 18. 2-(Ethoxycarbonylamino)-benzimidazole-1-carboximidic acid-(4-methylphenyl) ester | M.p. 128°decompn. |
| 19. 2-(Isopropoxycarbonylamino)-benzimidazole-1-carboximidic acid-(4-methylphenyl) ester | M.p. 130–133°C. |
| 20. 2-(Methoxycarbonylamino)-benzimidazole-1-carboximidic acid-(2,6-dimethylphenyl) ester | M.p. 157°C. decompn. |
| 21. 2-(Ethoxycarbonylamino)-benzimidazole-1-carboximidic acid-(2,6-dimethylphenyl) ester | M.p. 122°C. |
| 22. 2-(Isopropoxycarbonylamino)-benzimidazole-1-carboximidic acid-(2,6-dimethylphenyl) ester | M.p. 95°C |
| 23. 2-(Methoxycarbonylamino)-benzimidazole-1-carboximidic acid-(3,4-dimethylphenyl) ester | M.p. 210°C decompn. |
| 24. 2-(Ethoxycarbonylamino)-benzimidazole | |

-continued

| Compound according to invention | Physical constant |
|---|---|
| 1-carboximidic acid-(3,4,-dimethylphenyl) ester | M.p. 147°C decompn. |
| 25. 2-(Isopropoxycarbonylamino)-benzimidazole-1-carboximidic acid-(3,4-dimethylphenyl) ester | M.p. 139°C decompn. |
| 26. 2-(Methoxycarbonylamino)-benzimidazole-1-carboximidic acid-(2,4-dimethylphenyl) ester | M.p. 126°C decompn. |
| 27. 2-(Ethoxycarbonylamino)-benzimidazole-1-carboximidic acid-(2,4-dimethylphenyl) ester | M.p. 110°C decompn. |
| 28. 2-(Isopropoxycarbonylamino)-benzimidazole-1-carboximidic acid-(2,4-dimethylphenyl) ester | M.p. 110°C decompn. |
| 29. 2-(Methoxycarbonylamino)-benzimidazole-1-carboximidic acid-(2,4,6-trimethylphenyl) ester | M.p. 110°C decompn. |
| 30. 2-(Ethoxycarbonylamino)-benzimidazole 1-carboximidic acid-(2,4,6-trimethylphenyl) ester | M.p. 125°C decompn. |
| 31. 2-(Isopropoxycarbonylamino)-benzimidazole-1-carboximidic acid-(2,4,6-trimethylphenyl) ester | M.p. 115°C decompn. |
| 32. 2-(Methoxycarbonylamino)-benzimidazole-1-carboximidic acid-(2-ethylphenyl)ester | M.p. 120°C decompn. |
| 33. 2-(Methoxycarbonylamino)-benzimidazole-1-carboximidic acid-(2,4-dimethylphenyl) ester | M.p. 126°C decompn. |
| 34. 2-(Ethoxycarbonylamino)-benzimidazole 1-carboximidic acid-(2,4-dimethylphenyl) ester | M.p. 110°C decompn. |
| 35. 2-(Isopropoxycarbonylamino)-benzimidazole-1-carboximidic acid-(2,4-dimethylphenyl) ester | M.p. 110°C decompn. |
| 36. 2-(Methoxycarbonylamino)-benzimidazole-1-carboximidic acid-(2,4,6-trimethylphenyl) ester | M.p. 110°C decompn. |
| 37. 2-(Ethoxycarbonylamino)-benzimidazole-1-carboximidic acid-(2,4,6-trimethylphenyl) ester | M.p. 125°C decompn. |
| 38. 2-(Isopropoxycarbonylamino)-benzimidazole-1-carboximidic acid-(2,4,6-trimethylphenyl) ester | M.p. 115°C decompn. |
| 39. 2-(Methoxycarbonylamino)-benzimidazole-1-carboximidic acid-(2-ethylphenyl) ester | M.p. 120°C decompn. |
| 40. 2-(Ethoxycarbonylamino)-benzimidazole-1-carboximidic acid-(2-ethylphenyl) ester | M.p. 125°C decompn. |
| 41. 2-(Isopropoxycarbonylamino)-benzimidazole-1-carboximidic acid-(2-ethylphenyl) ester | M.p. 105°C decompn. |
| 42. 2-(Methoxycarbonylamino)-benzimidazole-1-carboximidic acid-(4-ethylphenyl) ester | M.p. 140°C decompn. |
| 43. 2-Ethoxycarbonylamino)-benzimidazole-1-carboximidic acid-(4-ethylphenyl) ester | M.p. 165°C decompn. |
| 44. 2-(Isopropoxycarbonylamino)-benzimidazole-1-carboximidic acid-(4-ethylphenyl) ester | M.p. 95°C |
| 45. 2-(Methoxycarbonylamino)-benzimidazole-1-carboximidic acid-(2-isopropylphenyl) ester | M.p. 130°C decompn. |
| 46. 2-(Ethoxycarbonylamino)-benzimidazole-1-carboximidic acid-(2-isopropylphenyl) ester | M.p. 115°C decompn. |
| 47. 2-(Isopropoxycarbonylamino)-benzimidazole-1-carboximidic acid-(2-isopropylphenyl) ester | M.p. 90°C |
| 48. 2-(Methoxycarbonylamino)-benzimidazole-1-carboximidic acid-(4-tert.-butylphenyl) ester | M.p. 163°C decompn. |
| 49. 2-(Ethoxycarbonylamino)-benzimidazole-1-carboximidic acid-(4-tert.-butylphenyl) ester | M.p. 155°C decompn. |
| 50. 2-(Isopropoxycarbonylamino)-benzimidazole-1-carboximidic acid-(4-tert.-butylphenyl)ester | M.p. 150°C decompn. |
| 51. 2-(Methoxycarbonylamino)-benzimidazole-1-carboximidic acid-(3-tert.-butylphenyl) ester | M.p. 100°C |
| 52. 2-(Ethoxycarbonylamino)-benzimidazole-1-carboximidic acid-(3-tert.-butylphenyl) ester | M.p. 65°C |
| 53. 2-(Isopropoxycarbonylamino)-benzimidazole-1-carboximidic acid-(3-tert.-butylphenyl) ester | M.p. 65°C |
| 54. 2-(Methoxycarbonylamino)-benzimidazole-1-carboximidic acid-(2-sec.-butyl- | |

-continued

| Compound according to invention | Physical constant |
|---|---|
| phenyl) ester | M.p. 115°C |
| 55. 2-(Ethoxycarbonylamino)-benzimidazole-1-carboximidic acid-(2-sec.-butyl-phenyl) ester | M.p. 65°C. |
| 56. 2-(Isopropoxycarbonylamino)-benzimidazole-1-carboximidic acid-(2-sec.-butylphenyl) ester | M.p. 95°C. |
| 57. 2-(Methoxycarbonylamino)-benzimidazole-1-carboximidic acid-(4-isoheptylphenyl) ester | M.p. 129°C decompn. |
| 58 2-(Methoxycarbonylamino)-benzimidazole-1-carboximidic acid-(4-nonylphenyl) ester | M.p. 80°C. |
| 59. 2-(Ethoxycarbonylamino)-benzimidazole-1-carboximidic acid-(4-nonylphenyl) ester | M.p. 135°C decompn. |
| 60. 2-(Methoxycarbonylamino)-benzimidazole-1-carboximidic acid-(4-biphenylyl) ester | M.p. 165°C decompn. |
| 61. 2-(Ethoxycarbonylamino)-benzimidazole-1-carboximidic acid-(4-biphenylyl) ester | M.p. 145°C decompn. |
| 62. 2-(Isopropoxycarbonylamino)-benzimidazole-1-carboximidic acid-(4-biphenylyl) ester | M.p. 85°C |
| 63. 2-(Methoxycarbonylamino)-benzimidazole-1-carboximidic acid-(1-naphthyl) ester | M.p. 150°C decompn. |
| 64. 2-(Ethoxycarbonylamino)-benzimidazole-1-carboximidic acid-(1-napthyl) ester | M.p. 144°C decompn. |
| 65. 2-(Isopropoxycarbonylamino)-benzimidazole-1-carboximidic acid-(1-naphthyl) ester | M.p. 142°C decompn. |
| 66. 2-(Methoxycarbonylamino)-benzimidazole-1-carboximidic acid-(2-naphthyl) ester | M.p. 160°C decompn. |
| 67. 2-(Ethoxycarbonylamino)-benzimidazole-1-carboximidic acid-(2-naphthyl) ester | M.p. 155°C decompn. |
| 68. 2-(Isopropoxycarbonylamino)-benzimidazole-1-carboximidic acid-(2-naphthyl) ester | M.p. 125°C decompn. |
| 69. 2-(Methoxycarbonylamino)-benzimidazole-1-carboximidic acid-(2-chlorophenyl ester | M.p. 161°C decompn. |
| 70. 2-(Ethoxycarbonylamino)-benzimidazole-1-carboximidic acid-(2-chlorophenyl ester | M.p. 155°C decompn. |
| 71. 2-(Isopropoxycarbonylamino)-benzimidazole-1-carboximidic acid-(2-chlorophenyl) ester | M.p. 125°C decompn. |
| 72. 2-(Methoxycarbonylamino)-benzimidazole-1-carboximidic acid-(4-chlorophenyl) ester | M.p. 84°C |
| 73. 2-(Ethoxycarbonylamino)-benzimidazole-1-carboximidic acid-(4-chlorophenyl) ester | M.p. 68°C |
| 74. 2-(Isopropoxycarbonylamino)-benzimidazole-1-carboximidic acid-(4-chlorophenyl) ester | M.p. 95°C |
| 75. 2-(Methoxycarbonylamino)-benzimidazole-1-carboximidic acid-(3-chlorophenyl) ester | M.p. 172°C decompn. |
| 76. 2-(Ethoxycarbonylamino)-benzimidazole-1-carboximidic acid-(3-chlorophenyl) ester | M.p. 146°C decompn. |
| 77. 2-(Isopropoxycarbonylamino)-benzimidazole-1-carboximidic acid-(3-chlorophenyl) ester | M.p. 123°C decompn. |
| 78. 2-(Methoxycarbonylamino)-benzimidazole-1-carboximidic acid-(4-fluorophenyl) ester | M.p. 158°C decompn. |
| 79. 2-(Ethoxycarbonylamino)-benzimidazole-1-carboximidic acid-(4-fluorophenyl) ester | M.p. 145°C decompn. |
| 80. 2-(Methoxycarbonylamino)-benzimidazole-1-carboximidic acid-(4-bromophenyl) ester | M.p. 140°C decompn. |
| 81. 2-(Ethoxycarbonylamino)-benzimidazole-1-carboximidic acid-(4-bromophenyl) ester | M.p. 170°C decompn. |
| 82. 2-(Methoxycarbonylamino)-benzimidazole-1-carboximidic acid-(4-chloro-3-methyl-phenyl) ester | M.p. 162°C |
| 83. 2-(Ethoxycarbonylamino)-benzimidazole-1-carboximidic acid-(4-chloro-3-methyl-phenyl) ester | M.p. 158°C decompn. |
| 84. 2-(Isopropoxycarbonylamino)-benzimidazole-1-carboximidic acid-(4-chloro-3-methylphenyl) ester | M.p. 131°C |
| 85. 2-(Methoxycarbonylamino)-benzimidazole-1-carboximidic acid-(2-chloro-5-methyl-phenyl) ester | M.p. 153°C decompn. |
| 86. 2-(Ethoxycarbonylamino)-benzimidazole-1-carboximidic acid-(2-chloro-5- | |

-continued

| Compound according to invention | Physical constant |
|---|---|
| methylphenyl) ester | M.p. 135°C decompn. |
| 87. 2-(Isopropoxycarbonylamino)-benzimidazole-1-carboximidic acid-(2-chloro-5-methylphenyl) ester | M.p. 132°C decompn. |
| 88. 2-(Methoxycarbonylamino)-benzimidazole-1-carboximidic acid-(4-chloro-2-methylphenyl) ester | M.p. 151°C decompn. |
| 89. 2-Ethoxycarbonylamino)-benzimidazole-1-carboximidic acid-(4-chloro-2-methylphenyl) ester | M.p. 161°C decompn. |
| 90. 2-(Isopropoxycarbonylamino)-benzimidazole-1-carboximidic acid-(4-chloro-2-methylphenyl) ester | M.p. 130°C decompn. |
| 91. 2-(Methoxycarbonylamino)-benzimidazole-1-carboximidic acid-(2-bromo-4-methylphenyl ester | M.p. 130°C decompn. |
| 92. 2-(Ethoxycarbonylamino)-benzimidazole-1-carboximidic acid-(2-bromo-4-methylphenyl) ester | M.p. 145°C decompn. |
| 93. 2-(Isopropoxycarbonylamino)-benzimidazole-1-carboximidic acid-(2-bromo-4-methylphenyl) ester | M.p. 95°C |
| 94. 2-(Methoxycarbonylamino)-benzimidazole-1-carboximidic acid-(3-methoxyphenyl) ester | M.p. 144°C decompn. |
| 95. 2-(Ethoxycarbonylamino)-benzimidazole-1-carboximidic acid-(3-methoxyphenyl) ester | M.p. 142°C decompn. |
| 96. 2-(Isopropoxycarbonylamino)-benzimidazole-1-carboximidic acid-(3-methoxyphenyl) ester | M.p. 120–21°C decompn. |
| 97. 2-(Methoxycarbonylamino)-benzimidazole-1-carboximidic acid-(4-methoxyphenyl) ester | M.p. 178°C decompn. |
| 98. 2-(Ethoxycarbonylamino)-benzimidazole-1-carboximidic acid-(4-methoxyphenyl) ester | M.p. 173°C decompn. |
| 99. 2-(Isopropoxycarbonylamino)-benzimidazole-1-carboximidic acid-(4-methoxyphenyl) ester | M.p. 163°decompn. |
| 100. 2-(Methoxycarbonylamino)-benzimidazole-1-carboximidic acid-(4-methylthiophenyl) ester | M.p. 168°C decompn. |
| 101. 2-(Ethoxycarbonylamino)-benzimidazole-1-carboximidic acid-(4-methylthiophenyl) ester | M.p. 157°C decompn. |
| 102. 2-(Isopropoxycarbonylamino)-benzimidazole-1-carboximidic acid-(4-methylphenyl) ester | M.p. 103°C |
| 103. 2-(Methoxycarbonylamino)-benzimidazole-1-carboximidic acid-(3-methyl-4-methylthiophenyl) ester | M.p. 135°C decompn. |
| 104. 2-(Ethoxycarbonylamino)-benzimidazole-1-carboximidic acid-(3-methyl-4-methylthiophenyl) ester | M.p. 164°C decompn. |
| 105. 2-Isopropoxycarbonylamino)-benzimidazole-1-carboximidic acid-(3-methyl-4-methylthiophenyl) ester | M.p. 150°C decompn. |
| 106. 2-(Methoxycarbonylamino)-benzimidazole-1-carboximidic acid-(4-allyl-2-methoxyphenyl) ester | M.p. 135°C decompn. |
| 107. 2-(Ethoxycarbonylamino)-benzimidazole-1-carboximidic acid-(4-allyl-2-methoxyphenyl) ester | M.p. 140°C decompn. |
| 108. 2-(Isopropoxycarbonylamino)-benzimidazole-1-carboximidic acid-(4-allyl-2-methoxyphenyl) ester | M.p. 117°C decompn. |
| 109. 2-(Methoxycarbonylamino)-benzimidazole-1-carboximidic acid-(4-ethoxycarbonylphenyl) ester | M.p. 164°C decompn. |
| 110. 2-(Ethoxycarbonylamino)-benzimidazole-1-carboximidic acid-(4-ethoxycarbonylphenyl) ester | M.p. 162°C decompn. |
| 111. 2-(Isopropoxycarbonylamino)-benzimidazole-1-carboximidic acid-(4-ethoxycarbonylphenyl) ester | M.p. 148°decompn. |
| 112. 2-(Methoxycarbonylamino)-benzimidazole-1-carboximidic acid-(4-formylphenyl) ester | M.p. 132°C decompn. |
| 113. 2-(Ethoxycarbonylamino)-benzimidazole-1-carboximidic acid-(4-formylphenyl) ester | M.p. 134°C decompn. |
| 114. 2-(Isopropoxycarbonylamino)-benzimidazole-1-carboximidic acid-(4-formylphenyl) ester | M.p. 120–25°C decompn. |
| 115. 2-(Methoxycarbonylamino)-benzimidazole-1-carboximidic acid-(3-acetylphenyl) ester | M.p. 147°C decompn |
| 116. 2-Ethoxycarbonylamino)-benzimidazole-1-carboximidic acid-(3-acetylphenyl) ester | M.p. 145°C decompn. |

| Compound according to invention | Physical constant |
|---|---|
| 117. 2-(Isopropoxycarbonylamino)-benzimidazole-1-carboximidic acid-(3-acetylphenyl) ester | M.p. 117°C |
| 118. 2-(Methoxycarbonylamino)-benzimidazole-1-carboximidic acid-(4-acetylphenyl) ester | M.p. 115°C |
| 119. 2-(Ethoxycarbonylamino)-benzimidazole-1-carboximidic acid-(4-acetylphenyl) ester | M.p. 120°C |
| 120. 2-(Isopropoxycarbonylamino)-benzimidazole-1-carboximidic acid-(4-acetylphenyl) ester | M.p. 95°C |
| 121. 2-(Methoxycarbonylamino)-benzimidazole-1-carboximidic acid-(4-acetamidophenyl) ester | M.p. 151°C decompn. |
| 122. 2-(Ethoxycarbonylamino)-benzimidazole-1-carboximidic acid-(4-acetamidophenyl) ester | M.p. 155°C decompn. |
| 123. 2-(Isopropoxycarbonylamino)-benzimidazole-1-carboximidic acid-(4-acetamidophenyl) ester | M.p. 135°C decompn. |
| 124. 2-(Methoxycarbonylamino)-benzimidazole-1-carboximidic acid-(3-dimethylaminophenyl) ester | M.p. 164°C decomp. |
| 125. 2-(Ethoxycarbonylamino)-benzimidazole-1-carboximidic acid-(3-dimethylaminophenyl) ester | M.p. 148°C decompn. |
| 126. 2-(Isopropoxycarbonylamino)-benzimidazole-1-carboximidic acid-(3-dimethylaminophenyl) ester | M.p. 87–93°C |
| 127. 2-(Methoxycarbonylamino)-benzimidazole-1-carboximidic acid-(3-trifluoromethylphenyl) ester | M.p. 169°C decompn. |
| 128. 2-(Ethoxycarbonylamino)-benzimidazole-1-carboximidic acid-(3-trifluoromethylphenyl) ester | M.p. 161°C decompn. |
| 129. 2-(Methoxycarbonylamino)-benzimidazole-1-carboximidic acid-(4-cyanophenyl) ester | M.p. 136°C decompn. |
| 130. 2-(Methoxycarbonylamino)-benzimidazole-1-carboximidic acid-(3-nitrophenyl) ester | M.p. 153°C decompn. |
| 131. 2-(Isopropoxycarbonylamino)-benzimidazole-1-carboximidic acid-3-nitrophenyl) ester | M.p. 105°C |
| 132. 2-(Methoxycarbonylamino)-benzimidazole-1-carboximidic acid-(4-nitrophenyl) ester | M.p. 132°C |
| 133. Bis(2-isopropoxycarbonylamino-benzimidazole-1-carboximidic acid)-m-phenylene diester | M.p. 125°C |
| 134. Bis(2-isopropoxycarbonylamino-benzimidazole-1-carboximidic acid)-p-phenylene diester | M.p. 100°C |
| 135. Bis(2-methoxycarbonylamino-benzimidazole-1-carboximidic acid)-m-phenylene-diester | M.p. 105°C decompn. |
| 136. Bis(2-methoxycarbonylamino-benzimidazole-1-carboximidic acid)-p-phenylene diester | M.p. 165°C |

The compounds of the invention are practically colorless and odorless crystalline substances. They are insoluble in water and benzine and more or less soluble in dimethyl sulfoxide, chloroform, acetone, dimethyl formamide and tetrahydrofurane.

The starting products for the manufacture of the compounds of the invention are known in themselves or can be produced by known methods.

The fungicidal effect of the compounds of the invention in comparison to known agents will become evident from the following examples.

EXAMPLE 1

The fungicidal effect of the compounds of the invention was tested against plant pathogenic fungi on artificial culture medium in Petri dishes (agar impregnation test). A culture medium consisting of 2% malt extract and 1.5% agar-agar powder was sterilized and thoroughly mixed with the compounds to be tested before solidification, so that the medium contained the active substances listed in the table in the different quantities of 9.3 and 1 ppm, respectively. After the medium had solidified, it was inoculated with a platinum dropper containing about 100 spores of the fungus to be tested. After exposure for 5 to 10 days at 22°C, the diameters of the fungus colonies in mm were measured. The diameter of the colonies on untreated culture media (control) was taken as 100. The diameter of the colonies on the untreated [sic] media was stated in relation to the control (relative per cent).

|   | Compound According to Invention | Diameter of the colonies (Relative per cent at control = 100) | | | | | | | | |
|---|---|---|---|---|---|---|---|---|---|---|
|   |   | Botrytis cinerea | | | Colletotrichum gloeospor. | | | Penicillium spec. | | |
|   |   | 9 | 3 | 1 | 9 | 3 | 1 | 9 | 3 | 1 ppm |
| 1. | 2-(Methoxycarbonylamino)-benzimidazole-1-carboximidic acid phenyl ester | — | 15 | 18 | — | 0 | 0 | — | 0 | 0 |
| 2. | 2-(Methoxycarbonylamino)-benzimidazole-1-carboximidic acid-(4-methylphenyl) ester | — | 13 | 18 | — | 0 | 0 | — | 0 | 0 |
| 3. | 2-(Methoxycarbonylamino)-benzimidazole-1-carboximidic acid-(3-methylphenyl) ester | — | 10 | 16 | — | 0 | 0 | — | 0 | 0 |
| 4. | 2-(Isopropoxycarbonylamino)-benzimidazole-1-carboximidic acid-(4-chloro-3-methylphenyl) ester | — | 13 | 18 | — | 0 | 14 | — | 0 | 15 |
| 5. | 2-(Methoxycarbonylamino)-benzimidazole-1-carboximidic acid-(3-dimethylaminophenyl) ester | — | 11 | 18 | — | 0 | 0 | — | 0 | 0 |
| 6. | 2-(Methoxycarbonylamino)-benzimidazole-1-carboximidic acid-(4-nonylphenyl) ester | — | 11 | 18 | — | 0 | 0 | — | 0 | 0 |
|   | Comparison Agent |   |   |   |   |   |   |   |   |   |
| 7. | N-(trichloromethylthio)-phthalimide | 0 | 32 | 72 | 0 | 0 | 78 | 20 | 79 | 88 |
|   | Control (Untreated) |   | 100 |   |   | 100 |   |   | 100 |   |

EXAMPLE 2

Young squash plants with fully developed cotyledons were placed in aqueous suspensions of 40 ppm each of the substances to be tested. The young plants stood in the suspensions only so far that the roots and a piece of stem at most 5 mm long (hypocotyl) were in the liquid. After 24 hours the plants were taken out of the suspensions, rinsed, and sterilized externally. From the upper end of the hypocotyl, directly under the attachment of the cotyledons, a piece of stem about 3 mm long was cut out. The total length of the hypocotyl was about 50 mm. The stem pieces were placed in sterile Petri dishes with the cut surface on a malt extract agar which had been well mixed with spores of Botrytis cineres before solidification. Two days after the laying out of the stem pieces, the diameter of the inhibition haloes formed around the stem pieces (no growth of Botrytis) was determined. The size of the inhibition haloes indicates the rate of propagation and the intensity of action.

| Compound According to Invention | Diameter of the Inhibition haloes in mm after exposure to 40 ppm for 24 hours |
|---|---|
| 1. 2-(Ethoxycarbonylamino)-benzimidazole-1-carboximidic acid-(3-methylphenyl) ester | 18 |
| 2. 2-(Methoxycarbonylamino)-benzimidazole-1-carboximidic acid-(2,4-dimethylphenyl) ester | 19 |
| 3. 2-(Ethoxycarbonylamino)-benzimidazole-1-carboximidic acid-(2,4-dimethylphenyl) ester | 17 |
| 4. 2-(Isopropoxycarbonylamino)-benzimidazole-1-carboximidic acid-(2,4-dimethylphenyl) ester | 15 |
| 5. 2-(Methoxycarbonylamino)-benzimidazole-1-carboximidic acid-(3-trifluoromethylphenyl) ester | 17 |
| 6. 2-(Isopropoxycarbonylamino)-benzimidazole-1-carboximidic acid-(4-methoxyphenyl) ester | 16 |
| 7. 2-(Methoxycarbonylamino)-benzimidazole-1-carboximidic acid-(4-methoxyphenyl) ester | 19 |
| 8. 2-(Methoxycarbonylamino)-benzimidazole-1-carboximidic acid-(2-naphthyl) ester | 22 |
| 9. 2-(Methoxycarbonylamino)-benzimidazole-1-carboximidic acid-(4-methylthiophenyl) ester | 22 |
| 10. 2-(Methoxycarbonylamino)-benzimidazole-1-carboximidic acid-(4-isoheptylphenyl) ester | 24 |
| 11. Methyl-1-(butylcarbamoyl)-2-benzimidazole carbamate | 11 |
| Control (Untreated) | 0 |

EXAMPLE 3

Wheat grains artificially contaminated with 3 g spores of Tilletia caries per kg of wheat were thoroughly mixed with the compounds listed in the table in the two application quantities of 100 and 50 ppm, respectively. To obtain a uniform distribution of the active substance on the grain, the compounds to be tested were provided with the usual additions such as kaolin, talc, chalk, colorant, oil, etc. After the treatment, the disinfected and undisinfected grains were stuck halfway into a mudded loam and kept at 10°C. After 6 days the grains were removed. On the 10th day the germination of the spores in the holes of the removed wheat grains was evaluated. The spore growth of the undisinfected grains (control) was taken as 100. The growth of the spores in the holes after removal of the treated grains was stated in relation to the control.

| Compound of Invention | % spore germination at 100 ppm | 50 ppm |
|---|---|---|
| 1. 2-(Methoxycarbonylamino)-benzimidazole-1-carboximidic acid-(4-methylphenyl) ester | 1.5 | 6 |
| 2. 2-(Ethoxycarbonylamino)-benzimidazole-1-carboximidic acid-(4-methylphenyl) ester | 1.5 | 3 |
| 3. 2-(Methoxycarbonylamino)-benzimidazole-1-carboximidic acid-(3-methylphenyl) ester | 1.5 | — |
| 4. 2-(Isopropoxycarbonylamino)-benzimidazole-1-carboximidic acid-)4-chlorophenyl) ester | 0.3 | 15 |
| 5. 2-(Methoxycarbonylamino)-benzimidazole-1-carboximidic acid-(3-acetylphenyl) ester | 0 | 0 |
| 6. 2-(Methoxycarbonylamino)-benzimidazole-1-carboximidic acid-(3-nitrophenyl) ester | 0 | 0 |
| 7. 2-(Methoxycarbonylamino)-benzimidazole-1-carboximidic acid-(2,2,2-tribromoethyl) ester | 0 | 0 |
| 8. 2-(Ethoxycarbonylamino)-benzimidazole-1-carboximidic acid-(4-fluorophenyl) ester | 0 | 0 |
| 9. 2-(Methoxycarbonylamino)-benzimidazole-1-carboximidic acid-(4-acetylphenyl) ester | 0 | 0 |
| 10. Bis(2-methoxycarbonylaminobenzimidazole-1-carboximidic acid)-m-phenylene diester | 0 | 0 |
| *Comparison Agent* | | |
| 11. Methoxyethyl-Hg-silicate | 7 | — |
| Control (Untreated) | 100 | |

EXAMPLE 4

Rye seed naturally contaminated with Fusarium nivale was thoroughly mixed with the compounds to be tested. To achieve a uniform distribution of the active substance on the grain, the compounds to be tested were provided with the usual additions such as kaolin, talc, chalk, dye, oil, etc. Then the seed was put in soil and exposed to a temperature of 6° to 12°C in an air-conditioned chamber. After about 4 weeks the percentual infection of the plants was determined. The infection of the control was taken as 100. The infection of the plants after treatment of the seed with the tested compounds was stated in relation to the control.

| Compound of Invention | % infecton at 12.5 ppm | 2.5 ppm | 0.5 ppm |
|---|---|---|---|
| 1. 2-(Isopropoxycarbonylamino)-benzimidazole-1-carboximidic acid phenyl ester | 0 | 15 | 82 |
| 2. 2-(Methoxycarbonylamino)-benzimidazole-1-carboximidic acid-(3-methylphenyl) ester | 0 | 0 | 86 |
| 3. 2-(Methoxycarbonylamino)-benzimidazole-1-carboximidic acid-(4-chloro-3-methylphenyl) ester | 0 | 0 | 72 |
| 4. 2-(Ethoxycarbonylamino)-benzimidazole-1-carboximidic acid-(4-methoxyphenyl) ester | 0 | 10 | 98 |
| 5. 2-(Ethoxycarbonylamino)-benzimidazole-1-carboximidic acid-(4-iso-heptylphenyl) ester | 0 | 0 | 94 |
| 6. 2-(Methoxycarbonylamino)-benzimidazole-1-carboximidic acid-(3-nitrophenyl) ester | 0 | 0 | 14 |
| 7. 2-(Methoxycarbonylamino)-benzimidazole-1-carboximidic acid-(4-acetylphenyl) ester | 0 | 2 | 23 |
| *Comparison Agent* | | | |
| 8. Methoxyethyl-Hg-silicate | 28 | 45 | 0 |
| Control (Untreated) | | 100 | |

EXAMPLE 5

Oat seed artificially contaminated with Ustilago avenae was thoroughly mixed with the substance to be tested. To obtain a uniform distribution of the active substance of the grain, the compounds to be tested were provided with the usual additives such as kaolin, talc, chalk, dye, oil, etc. Then the seed was placed in soil and grown in a greenhouse. After the panicles appeared, the percentual infection of the oat plants was determined. The infection of the control was taken as 100. The infection in the plants of the tested compounds was stated in relation to the control.

| Compound of Invention | % infection at 500 ppm | 250 ppm | 100 ppm |
|---|---|---|---|
| 1. 2-(Methoxycarbonylamino)-benzimidazole-1-carboximidic acid-(4-methylphenyl) ester | 11 | 69 | 89 |
| 2. 2-(Methoxycarbonylamino)-benz- | | | |

| Compound of Invention | 500 ppm | % infection at 250 ppm | 100 ppm |
|---|---|---|---|
| imidazole-1-carboximidic acid-(3-methylphenyl) ester | 2 | 40 | 87 |
| 3. 2-(Methoxycarbonylamino)-benzimidazole-1-carboximidic acid-(3-nitrophenyl) ester | 0 | 0 | 5 |
| 4. 2-(Methoxycarbonylamino)-benzimidazole-1-carboximidic acid(2,2,2-tribromoethyl) ester | 0 | 0 | 7 |

| Comparison Agent | 188 ppm | % infection at 125 ppm | 50 ppm |
|---|---|---|---|
| Methoxy-Hg-silicate | 15 | 23 | 49 |
| Control (Untreated) | | 100 | |

EXAMPLE 6

Young plants of Vicia faba were thoroughly sprayed with 100 ppm of the compounds to be tested. After the spray coating had dried, the leaflets of the plants were inoculated. The inocula were 5 mm diameter. They were pricked out of a Petri dish grown over with Pellicularia sasakii. The plants were then set up in an infection chamber at 27°C and 95 to 100% rel. humidity. After 4 to 5 days the evaluation was made according to the percentual intensity of infection of the inoculated leaves. The infection of the leaves not sprayed (control) was taken as 100. The infection of the leaves with the tested compounds was stated in relation to the control.

| Compound of Invention | % infection at 100 ppm |
|---|---|
| 1. 2-(Methoxycarbonylamino)-benzimidazole-1-carboximidic acid phenyl ester | 0 |
| 2. 2-(Methoxycarbonylamino)-benzimidazole-1-carboximidic acid-(4-methylphenyl) ester | 0 |
| 3. 2-(Methoxycarbonylamino)benzimidazole-1-carboximidic acid-(3-methylphenyl) ester | 0 |
| 4. 2-(Methoxycarbonylamino)-benzimidazole-1-carboximidic acid-(4-tert.-butylphenyl) ester | 0 |
| 5. 2-(Methoxycarbonylamino)-benzimidazole-1-carboximidic acid-(2-chlorophenyl) ester | 0 |
| 6. 2-(Methoxycarbonylamino)-benzimidazole-1-carboximidic acid-(3-chlorophenyl) ester | 0 |
| Comparison Agent | |
| 7. Methyl-1-(butylcarbamoyl)-2-benzimidazole carbamate | 35 |
| Control (Untreated) | 100 |

EXAMPLE 7

Young plants of Vicia faba were thoroughly sprayed with the compounds to be tested. After the spray coating had dried, the plants were infected with a spore suspension of Botrytis fabae and placed in an infection chamber at 25°C and 95 to 100% rel. humidity. After 2 days the infection of the plants was evaluated. The infection of the control plants was taken as 100. The infection on the plants of the tested compounds was stated in relation to the control.

| Compound of Invention | % infection at 25 ppm | 2.5 ppm |
|---|---|---|
| 2-(Methoxycarbonylamino)-benzimidazole-1-carboximidic acid-(3-nitrophenyl) ester | 9 | 23 |
| 2-(Methoxycarbonylamino)-benzimidazole-1-carboximidic acid-(4-cyanophenyl) ester | 15 | — |
| Comparison Agent | | |
| 1,2-Di-(3-methoxycarbonyl-2-thioureido)-benzene | 26 | 52 |
| Control (Untreated) | 100 | |

EXAMPLE 8

Young plants of sugar beets (Beta vulgaris) were thoroughly sprayed with the compounds to be tested, in concentrations of 50 and 2.5 ppm, respectively. After the spray coating had dried, the plants were infected with a spore suspension of Cercospora beticola and set up for 48 hours in infection chambers of 25° to 27°C and 95 to 100% rel. humidity. Thereafter they stood in the greenhouse at about 25°C until the leaf spots appeared. In evaluating the infection, the infection of the control was taken as 100. The infection of the leaves with the tested compounds was stated in relation to the control.

sent as 20% powder preparations, there followed without waiting period the seeding out of 25 grains of mar-

| Compound of Invention | % infection at | |
|---|---|---|
| | 50 ppm | 2.5 ppm |
| 1. 2-(Methoxycarbonylamino)-benzimidazole-1-carboximidic acid phenyl ester | 0 | 9 |
| 2. 2-(Methoxycarbonylamino)-benzimidazole-1-carboximidic acid-(4-methylphenyl) ester | 0 | 3 |
| 3. 2-(Methoxycarbonylamino)-benzimidazole-1-carboximidic acid-(3-methylphenyl) ester | 0.6 | 6 |
| 4. 2-(Isopropoxycarbonylamino)-benzimidazole-1-carboximidic acid-(4-tert.-butylphenyl) ester | 0.6 | 9 |
| 5. 2-(Methoxycarbonylamino)-benzimidazole-1-carboximidic acid-(4-methyl-thiophenyl) ester | 0 | 9 |
| 6. 2-(Methoxycarbonylamino)-benzimidazole-1-carboximidic acid-(4-fluorophenyl) ester | 0.3 | 15 |
| Control Agent | | |
| Manganese ethylene-1,2-bisdithiocarbamate | 15 | 67 |
| Control (Untreated) | | 100 |

EXAMPLE 9

*Rhizoctonia solani;* limit concentrations of the soil fungicidal effect.

Steamed compost soil was inoculated with mycelium of *Rhizoctonia solani.* After homogeneous mixing of the products with the infected soil, the products were presented as 20% powder preparations, there followed without waiting period the seeding out of 25 grains of marrow peas of the variety "Miracle of Kelvedon." The cultivation time in the experiments was 20 to 23 days at a temperature of 22° to 25°C. Criteria in the evaluation are a sound root formation without fungus necrosis and at least 90% germination referred to the result attained in the steamed soil. Two commerical products were included in the test series as comparison agent.

| Rhizoctonia solani | |
|---|---|
| Limit concentrations of the soil-fungicidal effect determined until now (mg of active substance per liter of soil) | |
| 1. 2-(Methoxycarbonylamino)-benzimidazole-1-carboximidic acid-(3-methylphenyl) ester | 20 mg |
| 2. 2-(Methoxycarbonylamino)-benzimidazole-1-carboximidic acid phenyl ester | 20 mg |
| 3. 2-(Isopropoxycarbonylamino)-benzimidazole-1-carboximidic acid phenyl ester | 20 mg |
| 4. 2-(Ethoxycarbonylamino)-benzimidazole-1-carboximidic acid phenyl ester | 20 mg |
| 5. 2-(Methoxycarbonylamino)-benzimidazole-1-carboximidic acid-(2,2,2-trichloroethyl) ester | 40 mg |
| 6. 2-(Ethoxycarbonylamino)-benzimidazole-1-carboximidic acid-(2,2,2-trichloroethyl) ester | 40 mg |
| 7. 2-(Isopropoxycarbonylamino)-benzimidazole-1-carboximidic acid-(2,2,2-trichloroethyl) ester | 30 mg |
| 8. 2-(Methoxycarbonylamino)-benzimidazole-1-carboximidic acid-(2,2,2-trifluoroethyl) ester | 30 mg |
| 9. 2-(Ethoxycarbonylamino)-benzimidazole-1-carboximidic acid-(2,2,2-trifluoroethyl)-ester | 20 mg |
| 10. 2-(Isopropoxycarbonylamino)-benzimidazole-1-carboximidic acid-(2,2,2-trifluoroethyl)-ester | 30 mg |
| 11. 2-(Methoxycarbonylamino)-benzimidazole-1-carboximidic acid-(2,2,2-tribromoethyl) ester | 20 mg |
| 12. 2-(Ethoxycarbonylamino)-benzimidazole-1-carboximidic acid-(3-methylphenyl) ester | 20 mg |
| 13. 2-(Isopropoxycarbonylamino)-benzimidazole-1-carboximidic acid-(3-methylphenyl) ester | 20 mg |
| 14. 2-(Methoxycarbonylamino)-benzimidazole-1-carboximidic acid-(2-methylphenyl) ester | 30 mg |
| 15. 2-(Ethoxycarbonylamino)-benzimidazole-1-carboximidic acid-(2-methylphenyl) ester | 30 mg |
| 16. 2-(Isopropoxycarbonylamino)-benzimidazole-1-carboximidic acid-(2-methylphenyl) ester | 20 mg |
| 17. 2-(Methoxycarbonylamino)-benzimidazole-1-carboximidic acid-(4-methylphenyl) ester | 20 mg |
| 18. 2-(Ethoxycarbonylamino)-benzimidazole-1-carboximidic acid-(4-methylphenyl) ester | 20 mg |

-continued

Rhizoctonia solani
Limit concentrations of the soil-fungicidal effect determined
until now (mg of active substance per liter of soil)

| | |
|---|---|
| 19. 2-(Isopropoxycarbonylamino)-benzimidazole-1-carboximidic acid-(4-methylphenyl) ester | 20 mg |
| 20. 2-(Isopropoxycarbonylamino)-benzimidazole-1-carboximidic acid-(2,6-dimethylphenyl) ester | 40 mg |
| 21. 2-(Methoxycarbonylamino)-benzimidazole-1-carboximidic acid-(3,4-dimethylphenyl) ester | 40 mg |
| 22. 2-(Ethoxycarbonylamino)-benzimidazole-1-carboximidic acid-(3,4-dimethylphenyl) ester | 30 mg |
| 23. 2-(Isopropoxycarbonylamino)-benzimidazole-1-carboximidic acid-(3,4-dimethylphenyl) ester | 20 mg |
| 24. 2-(Methoxycarbonylamino)-benzimidazole-1-carboximidic acid-(2,4-dimethylphenyl) ester | 40 mg |
| 25. 2-(Ethoxycarbonylamino)-benzimidazole-1-carboximidic acid-(2,4-dimethylphenyl) ester | 30 mg |
| 26. 2-(Isopropoxycarbonylamino)-benzimidazole-1-carboximidic acid-(2,4-dimethylphenyl) ester | 20 mg |
| 27. 2-(Isopropoxycarbonylamino)-benzimidazole-1-carboximidic acid-(2,4,6-trimethylphenyl) ester | 20 mg |
| 28. 2-(Methoxycarbonylamino)-benzimidazole-1-carboximidic acid-(2-ethylphenyl) ester | 40 mg |
| 29. 2-(Ethoxycarbonylamino)-benzimidazole-1-carboximidic acid-(2-ethylphenyl) ester | 20 mg |
| 30. 2-(Isopropoxycarbonylamino)-benzimidazole-1-carboximidic acid-(2-ethylphenyl) ester | 20 mg |
| 31. 2-(Methoxycarbonylamino)-benzimidazole-1-carboximidic acid-(4-ethylphenyl) ester | 30 mg |
| 32. 2-(Ethoxycarbonylamino)-benzimidazole-1-carboximidic acid-(4-ethylphenyl) ester | 30 mg |
| 33. 2-Isopropoxycarbonylamino)-benzimidazole-1-carboximidic acid-(4-ethylphenyl) ester | 30 mg |
| 34. 2-(Methoxycarbonylamino)-benzimidazole-1-carboximidic acid-(2-isopropylphenyl) ester | 40 mg |
| 35. 2-(Ethoxycarbonylamino)-benzimidazole-1-carboximidic acid-(isopropylphenyl) ester | 20 mg |
| 36. 2-(Isopropoxycarbonylamino)-benzimidazole-1-carboximidic acid-(2-isopropylphenyl) ester | 20 mg |
| 37. 2-(Methoxycarbonylamino)-benzimidazole-1-carboximidic acid-(4-tert.-butylphenyl) ester | 30 mg |
| 38. 2-Ethoxycarbonylamino)-benzimidazole-1-carboximidic acid-(4-tert.-butylphenyl) ester | 40 mg |
| 39. Isopropoxycarbonylamino)-benzimidazole-1-carboximidic acid-(4-tert.-butylphenyl) ester | 30 mg |
| 40. 2-(Methoxycarbonylamino)-benzimidazole-1-carboximidic acid-(3-tert.-butylphenyl) ester | 20 mg |
| 41. 2-(Ethoxycarbonylamino)-benzimidazole-1-carboximidic acid-(3-tert.-butylphenyl) ester | 10 mg |
| 42. 2-(Isopropoxycarbonylamino)-benzimidazole-1-carboximidic acid-(3-tert.-butylphenyl) ester | 20 mg |
| 43. 2-(Ethoxycarbonylamino)-benzimidazole-1-carboximidic acid-(2-sec.-butylphenyl) ester | 20 mg |
| 44. 2-(Isopropoxycarbonylamino)-benzimidazole-1-carboximidic acid-(2-sec.-butylphenyl) ester | 30 mg |
| 45. 2-(Methoxycarbonylamino)-benzimidazole-1-carboximidic acid-(4-isoheptylphenyl) ester | 30 mg |
| 46. 2-(Ethoxycarbonylamino)-benzimidazole-1-carboximidic acid-(4-isoheptylphenyl) ester | 20 mg |
| 47. 2-(Methoxycarbonylamino)-benzimidazole-1-carboximidic acid-(4-nonylphenyl) ester | 30 mg |
| 48. 2-(Ethoxycarbonylamino)-benzimidazole-1-carboximidic acid-(4-nonylphenyl) ester | 50 mg |
| 49. 2-(Methoxycarbonylamino)-benzimidazole-1-carboximidic acid-(4-biphenyl) ester | 40 mg |
| 50. 2-(Ethoxycarbonylamino)-benzimidazole-1-carboximidic acid-(4-biphenyl) ester | 20 mg |
| 51. 2-(Isopropoxycarbonylamino)-benzimidazole-1-carboximidic acid-(4-biphenyl) ester | 20 mg |

-continued

Rhizoctonia solani
Limit concentrations of the soil-fungicidal effect determined
until now (mg of active substance per liter of soil)

| | |
|---|---|
| 52. 2-(Methoxycarbonylamino)-benzimidazole-1-carboximidic acid-(1-naphthyl) ester | 30 mg |
| 53. 2-(Ethoxycarbonylamino)-benzimidazole-1-carboximidic acid-(1-naphthyl) ester | 20 mg |
| 54. 2-(Isopropoxycarbonylamino)-benzimidazole-1-carboximidic acid-(1-naphthyl) ester | 20 mg |
| 55. 2-(Methoxycarbonylamino)-benzimidazole-1-carboximidic acid-(2-naphthyl) ester | 20 mg |
| 56. 2-(Ethoxycarbonylamino)-benzimidazole-1-carboximidic acid-(2-naphthyl) ester | 30 mg |
| 57. 2-(Isopropoxycarbonylamino)-benzimidazole-1-carboximidic acid-(2-naphthyl) ester | 20 mg |
| 58. 2-(Methoxycarbonylamino)-benzimidazole-1-carboximidic acid-(2-chlorophenyl) ester | 30 mg |
| 59. 2-(Ethoxycarbonylamino)-benzimidazole-1-carboximidic acid-(2-chlorophenyl) ester | 40 mg |
| 60. 2-(Isopropoxycarbonylamino)-benzimidazole-1-carboximidic acid-(2-chlorophenyl) ester | 20 mg |
| 61. 2-(Methoxycarbonylamino)-benzimidazole-1-carboximidic acid-(4-chlorophenyl) ester | 30 mg |
| 62. 2-(Ethoxycarbonylamino)-benzimidazole-1-carboximidic acid-(4-chlorophenyl) ester | 30 mg |
| 63. 2-(Isopropoxycarbonylamino)-benzimidazole-1-carboximidic acid-(4-chlorophenyl) ester | 20 mg |
| 64. 2-(Methoxycarbonylamino)-benzimidazole-1-carboximidic acid-(3-chlorophenyl) ester | 30 mg |
| 65. 2-(Ethoxycarbonylamino)-benzimidazole-1-carboximidic acid-(3-chlorophenyl) ester | 20 mg |
| 66. 2-(Isopropoxycarbonylamino)-benzimidazole-1-carboximidic acid-(3-chlorophenyl) ester | 20 mg |
| 67. 2-(Methoxycarbonylamino)-benzimidazole-1-carboximidic acid-(4-fluorophenyl) ester | 30 mg |
| 68. 2-(Ethoxycarbonylamino)-benzimidazole-1-carboximidic acid-(4-fluorophenyl) ester | 30 mg |
| 69. 2-(Methoxycarbonylamino)-benzimidazole-1-carboximidic acid-(4-bromophenyl) ester | 30 mg |
| 70. 2-(Ethoxycarbonylamino)-benzimidazole-1-carboximidic acid-(4-bromophenyl) ester | 50 mg |
| 71. 2-(Methoxycarbonylamino)-benzimidazole-1-carboximidic acid-(4-chloro-3-methyl-phenyl) ester | 30 mg |
| 72. 2-(Ethoxycarbonylamino)-benzimidazole-1-carboximidic acid-(4-chloro-3-methyl-phenyl) ester | 30 mg |
| 73. 2-(Isopropoxycarbonylamino)-benzimidazole-1-carboximidic acid-(4-chloro-3-methyl-phenyl) ester | 30 mg |
| 74. 2-(Methoxycarbonylamino)-benzimidazole-1-carboximidic acid-(2-chloro-5-methyl-phenyl) ester | 50 mg |
| 75. 2-(Ethoxycarbonylamino)-benzimidazole-1-carboximidic acid-(2-chloro-5-methyl-phenyl) ester | 20 mg |
| 76. 2-(Methoxycarbonylamino)-benzimidazole-1-carboximidic acid-(4-chloro-2-methylphenyl) ester | 50 mg |
| 77. 2-(Ethoxycarbonylamino)-benzimidazole-1-carboximidic acid-(4-chloro-2-methyl-phenyl) ester | 30 mg |
| 78. 2-(Isopropoxycarbonylamino)-benzimidazole-1-carboximidic acid-(4-chloro-2-methyl-phenyl) ester | 30 mg |
| 79. 2-(Methoxycarbonylamino)-benzimidazole-1-carboximidic acid-(2-bromo-4-methylphenyl) ester | 40 mg |
| 80. 2-(Isopropoxycarbonylamino)-benzimidazole-1-carboxylic acid-(2-bromo-4-methylphenyl) ester | 20 mg |
| 81. 2-(Methoxycarbonylamino)-benzimidazole-1-carboximidic acid-(3-methoxyphenyl) ester | 30 mg |
| 82. 2-(Ethoxycarbonylamino)-benzimidazole-1-carboximidic acid-(3-methoxyphenyl) ester | 20 mg |
| 83. 2-(Isopropoxycarbonylamino)-benzimidazole-1-carboximidic acid-(3-methoxyphenyl) ester | 20 mg |
| 84. 2-(Methoxycarbonylamino)-benzimidazole- | |

-continued

Rhizoctonia solani
Limit concentrations of the soil-fungicidal effect determined until now (mg of active substance per liter of soil)

| | |
|---|---|
| 1-carboximidic acid-(4-methoxyphenyl) ester | 20 mg |
| 85. 2-(Ethoxycarbonylamino)-benzimidazole-1-carboximidic acid-(4-methoxyphenyl) ester | 20 mg |
| 86. 2-(Isopropoxycarbonylamino)-benzimidazole-1-carboximidic acid-(4-methoxyphenyl) ester | 20 mg |
| 87. 2-(Methoxycarbonylamino)-benzimidazole-1-carboximidic acid-(4-methylthiophenyl) ester | 30 mg |
| 88. 2-(Ethoxycarbonylamino)-benzimidazole-1-carboximidic acid-(4-methylthiophenyl) ester | 30 mg |
| 89. 2-(Isopropoxycarbonylamino)-benzimidazole-1-carboximidic acid-(4-methylthiophenyl) ester | 20 mg |
| 90. 2-(Methoxycarbonylamino)-benzimidazole-1-carboximidic acid-(3-methyl-4-methylthiophenyl) ester | 30 mg |
| 91. 2-(Ethoxycarbonylamino)-benzimidazole-1-carboximidic acid-(3-methyl-4-methylthiophenyl) ester | 40 mg |
| 92. 2-(Isopropoxycarbonylamino)-benzimidazole-1-carboximidic acid-(3-methyl-4-methylthiophenyl) ester | 30 mg |
| 93. 2-(Ethoxycarbonylamino)-benzimidazole-1-carboximidic acid-(4-allyl-2-methoxyphenyl) ester | 40 mg |
| 94. 2-(Isopropoxycarbonylamino)-benzimidazole-carboximidic acid-(4-allyl-2-methoxyphenyl) ester | 20 mg |
| 95. 2-(Methoxycarbonylamino)-benzimidazole-1-carboximidic acid-(4-ethoxycarbonylphenyl) ester | 30 mg |
| 96. 2-(Ethoxycarbonylamino)-benzimidazole 1-carboximidic acid-(4-ethoxycarbonylphenyl) ester | 20 mg |
| 97. 2-(Isopropoxycarbonylamino)-benzimidazole-1-caboximidic acid-(4-ethoxycarbonylphenyl) ester | 30 mg |
| 98. 2-(Methoxycarbonylamino)-benzimidazole-1-carboximidic acid-(4-formylphenyl) ester | 40 mg |
| 99. 2-(Ethoxycarbonylamino)-benzimidazole-1-carboximidic acid-(4-formylphenyl) ester | 30 mg |
| 100. 2-(Isopropoxycarbonylamino)-benzimidazole-1-carboximidic acid-(4-formylphenyl) ester | 20 mg |
| 101. 2-(Methoxycarbonylamino)-benzimidazole-1-carboximidic acid-(3-acetylphenyl) ester | 30 mg |
| 102. 2-(Ethoxycarbonylamino)-benzimidazole-1-carboximidic acid-(3-acetylphenyl)-ester | 20 mg |
| 103. 2-(Ispropoxycarbonylamino)-benzimidazole-1-carboximidic acid-(3-acetylphenyl) ester | 20 mg |
| 104. 2-(Methoxycarbonylamino)-benzimidazole-1-carboximidic acid-(4-acetylphenyl) ester | 20 mg |
| 105. 2-(Ethoxycarbonylamino)-benzimidazole-1-carboximidic acid-(4-acetylphenyl) ester | 20 mg |
| 106. 2-(Isopropoxycarbonylamino)-benzimidazole-1-carboximidic acid-(4-acetylphenyl) ester | 40 mg |
| 107. 2-(Methoxycarbonylamino)-benzimidazole-1-carboximidic acid-(4-acetamidophenyl) ester | 20 mg |
| 108. 2-(Ethoxycarbonylamino)-benzimidazole-1-carboximidic acid-(4-acetamidophenyl) ester | 30 mg |
| 109. 2-(Isopropoxycarbonylamino)-benzimidazole-1-carboximidic acid-(4-acetamidophenyl) ester | 10 mg |
| 110. 2-(Methoxycarbonylamino)-benzimidazole-1-caboximidic acid-(3-dimethylaminophenyl) ester | 40 mg |
| 111. 2-(Ethoxycarbonylamino)-benzimidazole-1-carboximidic acid ester-(3-dimethylaminophenyl) ester | 30 mg |
| 112. 2-(Isopropoxycarbonylamino)-benzimidazole-1-carboximidic acid-(3-dimethylaminophenyl) ester | 30 mg |
| 113. 2-(Methoxycarbonylamino)-benzimidazole-1-carboximidic acid-(3-trifluoromethylphenyl) ester | 20 mg |
| 114. 2-(Ethoxycarbonylamino)-benzimidazole-1-carboximidic acid-(3-trifluoromethylphenyl) | |

-continued

Rhizoctonia solani
Limit concentrations of the soil-fungicidal effect determined until now (mg of active substance per liter of soil)

| | |
|---|---|
| ester | 30 mg |
| 115. 2-(Methoxycarbonylamino)-benzimidazole-1-carboximidic acid-(4-cyanophenyl) ester | 20 mg |
| 116. 2-(Methoxycarbonylamino)-benzimidazole-1-carboximidic acid-(3-nitrophenyl) ester | 10 mg |
| 117. 2-(Methoxycarbonylamino)-benzimidazole-1-caboximidic acid(4-nitrophenyl) ester | 20 mg |
| 118. Bis(2-isopropoxycarbonylamino-benzimidazole-1-carboximidic acid)-m-phenylene diester | 40 mg |
| 119. Bis(2-isopropoxycarbonylamino-benzimidazole-1-carboximidic acid)-p-phenylene diester | 10 mg |
| 120. Bis(2-methoxycarbonylamino-benzimidazole-1-carboximidic acid)-m-phenylene diester | 30 mg |
| 121. Bis(2-methoxycarbonylamino-benzimidazole-1-carboximidic acid)-p-phenylene diester | 20 mg |
| Comparison Agents | |
| 1,4-Dichloro-2,5-dimethoxybenzene | 30 mg |
| Pentachloronitrobenzene | 75 mg |

EXAMPLE 10

Steamed compost soil was inoculated with mycelium of *Rhizoctonia solani*. After homogeneous mixing of the products with the infected soil—the products were present as 20% powder preparations—there followed without waiting period the seeding out of 25 grains of marrow peas of the variety "Miracle of Kelvedon" per concentration in clay dishes holding 1 liter of soil. In the table is indicated the number of germinated sound peas, the fresh plant weight, and a root score after a cultivation time of 3 weeks at 22° to 25°C.

Root Score:
4 = white roots, without fungus necrosis
3 = white roots, slight fungus necrosis
2 = brown roots, more intense fungus necrosis
1 = intense fungus necrosis

| Compounds of Invention | mg active subst. per ltr. soil | Number of sound peas after 3 weeks | Fresh plant weight (g) | Root score (1–4) |
|---|---|---|---|---|
| 1. 2-(Ethoxycarbonylamino)-benzimidazole-1-carboximidic acid-(3-methylphenyl) ester | 10 mg | 3 | 2 g | 1 |
| | 20 mg | 25 | 24 g | 4 |
| | 30 mg | 22 | 24 g | 4 |
| 2. 2-(Isopropoxycarbonylamino)-benzimidazole-1-carboximidic acid-(3-methylphenyl) ester | 10 mg | 13 | 14 g | 2 |
| | 20 mg | 24 | 25 g | 4 |
| | 30 mg | 24 | 26 g | 4 |
| 3. 2-(Methoxycarbonylamino)-benzimidazole-1-carboximidic acid-(4-methylphenyl) ester | 10 mg | 13 | 14 g | 2 |
| | 20 mg | 23 | 24 g | 4 |
| | 30 mg | 25 | 24 g | 4 |
| 4. 2-(Isopropoxycarbonylamino)-benzimidazole-1-carboximidic acid-(4-methylphenyl) ester | 10 mg | 11 | 10 g | 3 |
| | 20 mg | 18 | 18 g | 4 |
| | 30 mg | 24 | 23 g | 4 |
| 5. 2-(Ispropoxycarbonylamino)-benzimidazole-1-carboximidic acid-(3,4-dimethylphenyl) ester | 10 mg | 3 | 2 g | 1 |
| | 20 mg | 25 | 21 g | 4 |
| | 30 mg | 22 | 19 g | 4 |
| 6. 2-(Isopropoxycarbonylamino)-benzimidazole-1-carboximidic acid-(2,4,6-trimethylphenyl) ester | 10 mg | 16 | 8 g | 2 |
| | 20 mg | 21 | 14 g | 3 |
| | 30 mg | 23 | 16 g | 4 |
| 7. 2-(Ethoxycarbonylamino)-benzimidazole-1-carboximidic acid-(2-isopropyphenyl) ester | 10 mg | 5 | 4 g | 1 |
| | 20 mg | 19 | 13 g | 4 |
| | 30 mg | 23 | 13 g | 4 |
| 8. 2-(Ethoxycarbonylamino)-benzimidazole-1-carboximidic acid-(3-tert.-butylphenyl ester | 10 mg | 22 | 15 g | 3 |
| | 20 mg | 23 | 12 g | 4 |
| | 30 mg | 24 | 12 g | 4 |
| 9. 2-(Ethoxycarbonylamino)-benzimidazole-1-carboximidic acid-(2-sec.-butylphenyl) ester | 10 mg | 7 | 4 g | 1 |
| | 20 mg | 23 | 23 g | 4 |
| | 30 mg | 22 | 19 g | 4 |
| 10. 2-(Ethoxycarbonylamino)-benzimid- | | | | |

| Compounds of Invention | mg active subst. per ltr. soil | Number of sound peas after 3 weeks | Fresh plant weight (g) | Root score (1–4) |
|---|---|---|---|---|
| azole-1-carboximidic acid-(4-isoheptylphenyl) ester | 10 mg | 8 | 5 g | 1 |
| | 20 mg | 21 | 17 g | 4 |
| | 30 mg | 25 | 21 g | 4 |
| 11. 2-(Ispropoxycarbonylamino)-benzimidazole-1-carboximidic acid-(1-naphthyl) ester | | | | |
| | 10 mg | 10 | 7 g | 3 |
| | 20 mg | 20 | 15 g | 4 |
| | 30 mg | 23 | 19 g | 4 |
| 12. 2-(Methoxycarbonylamino)-benzimidazole-1-carboximidic acid-(2-naphthyl) ester | | | | |
| | 10 mg | 6 | 4 g | 1 |
| | 20 mg | 24 | 18 g | 4 |
| | 30 mg | 23 | 19 g | 4 |
| 13. 2-(Ethoxycarbonylamino)-benzimidazole-1-carboximidic acid-(3-chlorophenyl) ester | | | | |
| | 10 mg | 5 | 4 g | 1 |
| | 20 mg | 19 | 16 g | 4 |
| | 30 mg | 22 | 20 g | 4 |
| 14. 2-(Isopropoxycarbonylamino)-benzimidazole-1-carboximidic acid-(3-chlorophenyl) ester | | | | |
| | 10 mg | 8 | 9 g | 2 |
| | 20 mg | 25 | 21 g | 4 |
| | 30 mg | 21 | 18 g | 4 |
| 15. 2-(Isopropoxycarbonylamino)-benzimidazole-1-carboximidic acid-(2-bromo-4-methylphenyl) ester | | | | |
| | 10 mg | 11 | 10 g | 3 |
| | 20 mg | 20 | 14 g | 4 |
| | 30 mg | 20 | 14 g | 4 |
| 16. 2-(Isopropoxycarbonylamino)-benzimidazole-1-carboximidic acid-(3-methoxyphenyl) ester | | | | |
| | 10 mg | 10 | 10 g | 3 |
| | 20 mg | 18 | 19 g | 4 |
| | 30 mg | 24 | 20 g | 4 |
| 17. 2-(Methoxycarbonylamino)-benzimidazole-1-carboximidic acid-(4-methoxyphenyl) ester | | | | |
| | 10 mg | 3 | 2 g | 1 |
| | 20 mg | 23 | 12 g | 3 |
| | 30 mg | 25 | 14 g | 4 |
| 18. 2-(Ethoxycarbonylamino)-benzimidazole-1-carboximidic acid-(4-methoxyphenyl) ester | | | | |
| | 10 mg | 5 | 2 g | 2 |
| | 20 mg | 24 | 14 g | 4 |
| | 30 mg | 23 | 16 g | 4 |
| 19. 2-(Ethoxycarbonylamino)-benzimidazole-1-carboximidic acid-(2,2,2-trifluoroethyl) ester | | | | |
| | 10 mg | 18 | 17 g | 3 |
| | 20 mg | 21 | 16 g | 4 |
| | 30 mg | 24 | 18 g | 4 |
| 20. 2-(Isopropoxycarbonylamino)-benzimidazole-1-carboximidic acid-(2-naphthyl) ester | | | | |
| | 10 mg | 10 | 6 g | 2 |
| | 20 mg | 25 | 20 g | 4 |
| | 30 mg | 24 | 19 g | 4 |
| 21. 2-(Isopropoxycarbonylamino)-benzimidazole-1-carboximidic acid-(4-methylthiophenyl) ester | | | | |
| | 10 mg | 11 | 9 g | 2 |
| | 20 mg | 23 | 20 g | 4 |
| | 30 mg | 25 | 21 g | 4 |
| 22. 2-(Isopropoxycarbonylamino)-benzimidazole-1-carboximidic acid-(4-acetamidophenyl) ester | | | | |
| | 10 mg | 21 | 13 g | 4 |
| | 20 mg | 21 | 16 g | 4 |
| | 30 mg | 23 | 19 g | 4 |
| 23. 2-(Methoxycarbonylamino)-benzimidazole-1-carboximidic acid-(4-cyanophenyl) ester | | | | |
| | 10 mg | 2 | 1 g | 1 |
| | 20 mg | 19 | 14 g | 4 |
| | 30 mg | 24 | 16 g | 4 |
| 24. 2-(Methoxycarbonylamino)-benzimidazole-1-carboximidic acid-(3-nitrophenyl) ester | | | | |
| | 10 mg | 23 | 14 g | 4 |
| | 20 mg | 23 | 16 g | 4 |
| | 30 mg | 23 | 18 g | 4 |
| 25. Bis(2-isopropoxycarbonylamino-benzimidazole-1-carboximidic acid)-p-phenylene diester | | | | |
| | 10 mg | 22 | 15 g | 4 |
| | 20 mg | 22 | 14 g | 4 |
| | 30 mg | 22 | 15 g | 4 |
| Comparison Agents | | | | |
| 1,4-Dichloro-2,5-dimethoxy-benzene | 10 mg | 0 | 0 g | 1 |
| | 20 mg | 0 | 0 g | 1 |
| | 25 mg | 10 | 9 g | 3 |
| | 30 mg | 21 | 18 g | 4 |
| | 40 mg | 24 | 24 g | 4 |
| Pentachloronitro-benzene | 50 mg | 4 | 4 g | 1 |
| | 100 mg | 25 | 15 g | 4 |
| Steamed soil | — | 21 | 18 g | 4 |

| Compounds of Invention | mg active subst. per ltr. soil | Number of sound peas after 3 weeks | Fresh plant weight (g) | Root score (1-4) |
|---|---|---|---|---|
| —continued | | | | |
| Untreated soil | — | 4 | 4 g | 1 |

EXAMPLE 11

Steamed compost soil was inoculated with mycelium of *Fusarium oxysporum f. callistephi*. After homogeneous mixing of the products with the infected soil, the products were present as 20% powder preparations—5 seedlings of *Callistephus chinensis*, Meisteraster "Sonnenstrahl" per concentration were set out without waiting period, as host plants. In the table is stated the number of infected plants after a cultivation time of 5 weeks at a temperature of 22°–25°C.

Fusarium oxysporum f. callistephi

| Compound | mg active subst. per liter soil | Number of infected plants after 5 weeks |
|---|---|---|
| 1. 2-(Ethoxycarbonylamino)-benzimidazle-1-carboximidic acid-(3-methylphenyl) ester | 20 mg | 0 |
| | 30 mg | 0 |
| 2. 2-(Ethoxycarbonylamino)-benzimidazole-carboximidic acid-(4-methylphenyl) ester | 20 mg | 1 |
| | 30 mg | 0 |
| 3. 2-(Ethoxycarbonylamino)-benzimidazole-1-carboximidic acid-(4-chlorophenyl) ester | 20 mg | 0 |
| | 30 mg | 0 |
| 4. 2-(Methoxycarbonylamino)-benzimidazole-1-carboximidic acid-(3-chlorophenyl) ester | 20 mg | 0 |
| | 30 mg | 0 |
| 5. 2-(Ethoxycarbonylamino)-benzimidazole-1-carboximidic acid-(3-methoxyphenyl) ester | 20 mg | 0 |
| | 30 mg | 0 |
| 6. 2-(Ethoxycarbonylamino)-benzimidazole-1-carboximidic acid-(4-ethoxycarbonylphenyl) ester | 20 mg | 1 |
| | 30 mg | 0 |
| 7. 2-(Ethoxycarbonylamino)-benzimidazole-1-carboximidic acid-(3-trifluoromethylphenyl) ester | 20 mg | 0 |
| | 30 mg | 0 |
| 8. 2-(Methoxycabonylamino)-benzimidazole-1-carboximidic acid-(3-nitrophenyl) ester | 20 mg | 0 |
| | 30 mg | 0 |
| Comparison Agent | | |
| Methyl-1-(butylcarbamoyl)-2-benzimidazole carbamate | 20 mg | 6 |
| | 30 mg | 3 |
| Steamed Soil | — | 0 |
| Untreated soil | — | 6 |

The superior insecticidal effect of the compounds of the invention in comparison to the fungicides of the benzimidazole series already widely in use in the practice, methyl-1-(butylcarbamoyl)-2-benzimidazole carbamate, is evidenced by the following examples:

EXAMPLE 12

Cut shoots of bush beans (*Phaseolus vulgaris*) in the fully developed primary leaf stage were dipped into aqueous suspensions with different content of compounds according to the invention. After the excess liquid had dripped off and the remaining coating had dried, the shoots were covered with six larvae (L3) per test member of the Mexican bean beetle (*Epilachna varivestis* Muls.). In checking the result after a three-day exposure, the achieved percentual effect was calculated according to Abbott. The test results can be read from the table below:

| Compound of Invention | Active subst. Concentration in % | Effect in % |
|---|---|---|
| 1. 2-(Ethoxycarbonylamino)-benzimidazole-1-carboximidic acid-(3,4-dimethylphenyl) ester | 0.1 | 100 |
| | 0.05 | 94 |
| 2. 2-(Isopropoxycarbonylamino)-benzimidazole-1-caboximidic acid-(3,4-dimethylphenyl) ester | 0.1 | 100 |
| | 0.05 | 60 |
| 3. 2-(Methoxycarbonylamino)-benzimidazole-1-carboximidic acid-(3,4-dimethylphenyl) ester | 0.1 | 67 |
| | 0.05 | 56 |
| 4. 2-(Methoxycarbonylamino)-benzimidazole-1-carboximidic acid-(2,4-dimethylphenyl) ester | 0.1 | 78 |
| 5. 2-(Ethoxycarbonylamino)-benzimidazole-1-carboximidic acid-(2,4-dimethylphenyl) ester | 0.1 | 100 |
| | 0.05 | 61 |
| 6. 2-(Isopropoxycarbonylamino)-benzimidazole-1-carboximidic acid-(2,4-dmethylphenyl) ester | 0.1 | 67 |
| | 0.05 | 50 |
| 7. 2-(Methoxycabonylamino)-benzimidazole-1-carboximidic acid-(3-tert.-butylphenyl) ester | 0.1 | 100 |
| | 0.05 | 100 |
| 8. 2-(Isopropoxycarbonylamino)-benzimidazole-1-carboximidic acid-(3-tert.-butylphenyl) ester | 0.1 | 100 |

| Compound of Invention | Active subst. Concentration in% | Effect in % |
|---|---|---|
| 9. 2-(Ethoxycarbonylamino)-benzimidazole-1-carboximidic acid-(2-methylphenyl) ester | 0.05 | 100 |
| | 0.1 | 100 |
| 10. 2-(Methoxycarbonylamino)-benzimidazole-1-carboximidic acid-(2-(1-methylpropyl)-phenyl) ester | 0.05 | 100 |
| | 0.1 | 61 |
| 11. 2-(Isopropoxycarbonylamino)-benzimidazole-1-carboximidic acid-(2-(1 methylpropyl)-phenyl) ester | 0.1 | 100 |
| | 0.05 | 100 |
| 12. 2-(Methoxycarbonylamino)-benzimidazole-1-carboximidic acid-(2-isopropylphenyl) ester | 0.01 | 94 |
| | 0.05 | 89 |
| 13. 2-(Isopropoxycarbonylamino)-benzimidazole-1-carboximidic acid-(2-isopropylphenyl) ester | 0.1 | 100 |
| | 0.05 | 72 |
| Comparison Agent | | |
| Methyl-1-(butylcarbamoyl)-2-benzimidazole carbamate | 0.1 | 34 |
| | 0.05 | 0 |

EXAMPLE 13

Potted single plants of *Vicia faba* were treated, after colonization with wingless individuals of *Aphis fabae* Scop., with aqueous suspensions of different concentrations of the compounds according to invention until the spray liquid began to drip off. In result controls after 48-hour tests the percentual action was determined. The results are summarized in the following table.

| Compound of Invention | Active Subst. Concentration in % | Effect in % |
|---|---|---|
| 1. 2-(Methoxycarbonylamino)-benzimidazole-1-carboximidic acid-(2-methylphenyl) ester | 0.1 | 100 |
| 2. 2-(Isopropoxycarbonylamino)-benzimidazole-1-carboximidic acid-(2-(1-methyl-propyl)-phenyl) ester | 0.1 | 100 |
| | 0.05 | 100 |
| 3. 2-(Methoxycarbonylamino)-benzimidazole-1-carboximidic acid-(2-isopropylphenyl) ester | 0.1 | 100 |
| | 0.05 | 100 |
| 4. 2-(Isopropoxycarbonylamino)-benzimidazole-1-carboximidic acid-(2-isopropylphenyl) ester | 0.1 | 100 |
| | 0.05 | 100 |
| Comparison Agent | | |
| 5. Methyl-1-(butylcarbamoyl)-2-benzimidazole carbamate | 0.1 | 80 |
| | 0.05 | 40 |

EXAMPLE 14

After proportioned spray treatment (400 ltr/ha) of oak shoots in foliage with aqueous suspensions of the compounds according to invention and drying of the spray coating, five caterpillars (L4) of *Porthetria dispar* L. per test member, separately treated in the same manner, were placed on the feed plant. After three-day exposure the percentual effect was determined according to Abbott. The test results are evident from the following table:

| Compound of Invention | Active subst. Concentration in % | Effect in % |
|---|---|---|
| 1. 2-(Ethoxycarbonylamino)-benzimidazole-1-carboximidic acid-(3-tert.-butylphenyl) ester | 0.2 | 100 |
| 2. 2-(Isopropoxycarbonylamino)-benzimidazole-1-carboximidic acid-(3 tert.-butylphenyl) ester | 0.2 | 100 |
| 3. 2-(ethoxycarbonylamino)-benzimidazole-1-carboximidic acid-(2-methylphenyl) ester | 0.2 | 100 |
| 4. 2-(Isopropoxycarbonylamino)-benzimidazole-1-carboximidic acid-(2-(1-methylpropyl)-phenyl) ester | 0.2 | 100 |

| Compound of Invention | -continued Active subst. Concentration in % | Effect in % |
|---|---|---|
| Comparison Agent | | |
| 5. Methyl-1-(butylcarbamoyl)-2-benzimidazole carbamate | 0.2 | 0 |

We claim:
1. A compound of the formula

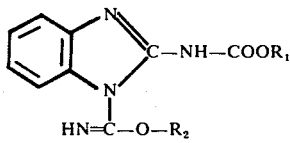

in which $R_1$ is alkyl or alkenyl each having from 1 to 4 carbons and $R_2$ is selected from the group consisting of trihalolower alkyl, phenyl, naphthyl, phenyl mono-, di-, or tri-substituted with alkyl or alkenyl each having from 1 to 12 carbons, cyclohexyl, lower alkoxy, lower alkylthio, lower alkoxycarbonyl, lower alkanoyl, lower alkanoylamino, di lower-alkylamino, trifluoromethyl, nitro, nitrile, halo, or the radicals

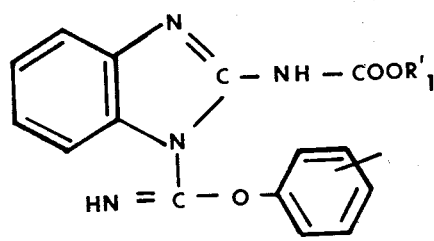

wherein $R'_1$ is methyl, ethyl, or isopropyl.

2. A benzimidazole-1-carboximidic acid ester according to claim 1, in which
$R_1$ is methyl, ethyl or isopropyl and
$R_2$ is 2,2,2-trifluoroethyl, 2,2,2-trichloroethyl, 2,2,2-tribromoethyl, phenyl, methylphenyl, dimethylphenyl, trimethylphenyl, ethylphenyl, isopropylphenyl, tert.-butylphenyl, sec.-butylphenyl, isoheptylphenyl, nonylphenyl, biphenyl, naphthyl, chlorophenyl, fluorophenyl, bromophenyl, chloromethylphenyl, bromomethyl-phenyl, methoxyphenyl, methylthiophenyl, methyl-methylthiophenyl, allylmethoxyphenyl, ethoxycarbonylphenyl, formylphenyl, acetylphenyl, acetamidophenyl, dimethylamino-phenyl, trifluoromethylphenyl, cyanophenyl, nitrophenyl or the radical

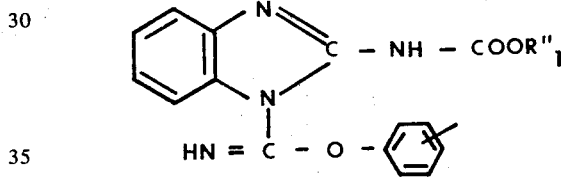

in which $R''_1$ has the meaning of methyl, ethyl or isopropyl.

* * * * *